United States Patent [19]

Woog et al.

[11] 4,191,772

[45] Mar. 4, 1980

[54] INSTILLATION COMPOSITION

[75] Inventors: Heinrich Woog, Laudenbach; Werner Gruber, Birkenau; Werner Rothe, Hackenheim, all of Fed. Rep. of Germany

[73] Assignee: Boehringer Mannheim GmbH, Mannheim, Fed. Rep. of Germany

[21] Appl. No.: 881,261

[22] Filed: Feb. 24, 1978

[30] Foreign Application Priority Data

Mar. 30, 1977 [DE] Fed. Rep. of Germany ....... 2714065

[51] Int. Cl.$^2$ ................ A61K 31/435; A61K 31/415; A61K 31/44
[52] U.S. Cl. ................................. 424/273 R; 424/256
[58] Field of Search ..................... 424/168, 172, 273

[56] References Cited

U.S. PATENT DOCUMENTS

| | | | |
|---|---|---|---|
| 1,890,860 | 12/1932 | Omohundro | 424/168 |
| 3,492,399 | 1/1970 | Prigal | 424/168 |

OTHER PUBLICATIONS

Goodman et al., "The Pharmacological Basis of Therapeutics", McMillan Co. (1955) p. 1118.

*Primary Examiner*—Albert T. Meyers
*Assistant Examiner*—H. Steven Seifert
*Attorney, Agent, or Firm*—Sprung, Felfe, Horn, Lynch & Kramer

[57] ABSTRACT

An instillation composition, comprising an effective amount of at least one sparingly soluble active material suspended or partly dissolved in an aqueous emulsion containing a swelling agent. Advantageously the active substance is nitrofurantoin or a quinolone or pyridazine derivative, the active material has a particle size less than about 10 $\mu$m and the swelling agent is a polysaccharide derivative present in about 0.3 to 3% by weight of the composition, the composition further containing at least one local anesthetic, antiphlogistic substance, emulsifier, buffer or stabilizer. With the invention, unit doses of only 50 ml. will contain sufficient active material.

4 Claims, No Drawings

INSTILLATION COMPOSITION

The present invention is a directly usable, stable, readily compatible instillation emulsion composition which contains at least one sparingly soluble substance as the active material.

The active material present in compositions according to the present invention is preferably an antibacterial substance, for example nitrofurantoin or a quinolone or pyridazine derivative. The active material can be partly dissolved in one or both phases of the emulsion and can be present suspended in the emulsion.

The chemotherapeutic substance nitrofurantoin has long been used therapeutically in the form of an instillation composition. Because of its low solubility in water, the composition was hitherto made by dissolving nitrofurantoin in 20 ml. polyethylene glycol and putting it on the market in an ampule. In order to prepare the final instillation solution, the content of the ampule must be diluted with water to 200 ml. This can be very time consuming since the physician using it must take care to carry out the dilution with water of satisfactory purity according to the given instructions in appropriately clean vessels. Furthermore, a volume of 200 ml. has to be introduced into the bladder, which is not very pleasant for the patient.

If it is desired to administer the nitrofurantoin in the amount necessary to achieve a therapeutic effect dissolved in a volume of about 50–100 ml., then a comparatively high proportion of organic solvent is needed because, for example, in 100 ml. water at pH 7.0, the maximum of nitrofurantoin which will dissolve is 11.4 mg. In high concentrations, these organic solvents attack the mucous membranes of the urinary tract so that such compositions do not have an optimum compatibility.

The same problem also exists for other sparingly soluble active materials, such as pyridazine or quinolone derivatives, for example nalidixic acid.

It is accordingly an object of the present invention to provide an installation composition containing a relatively high concentration of sparingly soluble active material.

This object is realized in accordance with the present invention wherein there is provided an instillation composition comprising at least one sparingly soluble active material suspended or partly dissolved in an emulsion, together with the addition of a swelling agent.

Emulsions have proved to be especially readily compatible for administration by instillation. However, in the case of the instillation composition according to the present invention, the whole amount of the active material is not, as is usual, present in dissolved form: on the contrary, the solid active material is at least partly suspended in micronized form in a liquid carrier which contains a swelling agent. The liquid carrier used can be an oil-in-water or water-in-oil emulsion. The particle size of the active material is preferably less than about 10 μm.

The therapeutic advantages of the composition according to the present invention are due, inter alia, to the good adhesion of the emulsion to mucous membranes and the slow dissolving of the active material particles at the desired place of action, a good compatibility and a prolonged action thereby being ensured.

The present invention provides for the first time, a directly usable and readily compatible emulsion instillation composition which contains a suspension of sparingly soluble, medicinally effective solid material particles in the form of a stable composition.

It is known that solid material particles, especially in the case of liquid emulsions, cause the phase separation of the two liquid emulsion components and thus reduce the stability of the emulsion (cf. Münzel-Büchi, Galenisches Praktikum, 1959 edition, pages 398–400). Surprisingly, the emulsion can be stabilized by incorporating a swelling agent into the emulsion. The swelling agent also improves the compatibility of the emulsion and has a further positive effect:

When a solid material is suspended in an emulsion, then, upon storage or in the case of variations in temperature, a certain proportion thereof dissolves in the two phases of the emulsion and the amount thereof dissolved in the two emulsion phases can differ. Temperature variations can also result in the crystallizing out of the active material. If, however, a swelling agent is incorporated into the emulsion, an improved stability of the crystal suspension is achieved and crystal growth is prevented. This is very important because, for example, when nitrofurantoin crystallizes out, needle-shaped crystals of up to 300 μm. length can result which, upon instillation, can cause damage to the mucous membranes of the urinary tract.

An important advantage of the instillation composition of the present invention is that it is present in a relatively small volume. Thus, for example, in the case of nitrofurantoin, there can be used a volume of 50 ml., which is preferably packed in a siphon flask made, for example, of polyethylene, and which can be instilled directly without dilution. In comparison with the known nitrofurantoin instillation compositions which must be diluted, there is thus achieved a saving of time, as well as a reduced danger of contamination.

Furthermore, the composition according to the present invention guarantees an intensive and long-lasting adhesion to the mucous membranes and thereby ensures an optimum therapeutic action.

If desired, the new composition can also contain a local anaesthetic and/or antiphlogistic agent. The local anaesthetic can be, for example, Xylocaine (lidocaine) (2-diethylamino-N-(2,6-dimethylphenyl)-acetamide), tetracaine (β-dimethylaminoethyl p-butylamino-benzoate) or anesthesin (ethyl p-amino-benzoate) and the antiphlogistic agent can be, for example, betamethasone, dexamethasone or fluorometholone. Up to about 0.05% and preferably about 0.01 to 0.04% by weight of the composition is suitable.

As swelling agent, there can be used a conventional polysaccharide derivative, such as methyl cellulose (Culminal K 42), sodium carboxymethylcellulose (Tylose C 1000 p) or a galacturonic acid-containing polysaccharide (tragacanth). The amount of swelling agent in the composition according to the present invention can, depending upon the nature of the swelling agent, be about 0.3 to 3% by weight, referred to the weight of the composition as a whole. Other polymers which swell in aqueous liquids, especially of the composition encountered in the urinary tract, can similarly be employed.

The emulsion composition according to the present invention can be prepared by any of the usual processes used for the distribution of water in oil and of oil in water, such as stirring with high speed mechanical stirrers, ultra-sonics, shaking, injection into the other liquid or the like, with the addition of emulsifiers and possibly with warming (cf. Römpps Chemie-Lexikon, 7th edition, page 1009).

The oil-in-water emulsion preferably contains about 0.5 to 10% by weight of a non-ionic emulsifier or about 0.1 to 5% of an ionic emulsifier, for example polyoxyethylene stearate (Myrj 52, Tegin or Protegin X).

The lipophilic phase, as well as the emulsifier, must have a good compatibility with mucous membranes. The proportion of lipophilic phase is preferably from 10 to 30% by weight and the non-ionic emulsifier can replace a part of the oily phase. The oily phase is preferably Miglyol 812 but all other oils which have a good compatibility with mucous membranes can also be used, for example olive oil or sesame oil. The proportion of the aqueous phase is preferably about 60 to 90%. If desired, an additional buffer and/or stabilizer can also be added.

In the case of water-in-oil emulsions, the lipophilic phase can be, for example, a non-ionic emulsifier in an amount of about 20 to 50% by weight and oily fats in an amount of about 3-15% by weight and, as hydrophilic phase, there can be used, for example, glycerol or polyethylene glycol 400 in an amount of about 3 to 15% by weight, together with about 35-65% by weight of water.

The following examples are given for the purpose of illustrating the present invention, the percentages being by weight:

EXAMPLE 1.

Oil-in-water emulsion systems 0.1–0.5% of nitrofurantoin monohydrate with a particle size of <10 μm. is suspended in 0.5–10% of a non-ionic or 0.1–5% of an ionic oil-in-water emulsifier, with the addition of polyethylene glycol and of an appropriate lipophilic phase, this suspension being emulsified in 60 to 80% of water, in which a swelling material has been pre-swollen, by stirring and possibly warming. There is thus obtained a stable oil-in-water emulsion which can be administered by instillation.

The formulations given in the following Table 1 have proved to be especially useful:

TABLE 1

| Component | Amount | | | | | | |
|---|---|---|---|---|---|---|---|
| | A | B | C | D | E | F | G |
| Nitrofurantoin monohydrate | 100.0 mg | 100.0 mg | 100.0 mg | 100.0 mg | 100.0 mg | 100.0 mg | 100.0 mg |
| Polyethylene glycol 400 | 5.62 g | — | 20.0 g | 15.0 g | 15.0 g | 15.0 g | 15.0 g |
| Miglyol 812 (oily triglyceride mixture of low viscosity) | 4.75 g | 4.75 g | 5.0 g | 10.0 g | 10.0 g | 10.0 g | 10.0 g |
| Tylose C 100 p (carboxymethyl cellulose) | 0.5 g | 0.5 g | — | — | — | — | — |
| Myrj 52 (polyoxyethylene stearate) | 0.5 g | 0.5 g | 0.5 g | — | — | — | — |
| Tegin (glycerol stearates) | — | — | — | 1.0 g | 2.5 g | 5.0 g | 7.5 g |
| Culminal K 42 (methyl cellulose) | — | — | 0.4 g | 0.3 g | 0.3 g | 0.3 g | 0.3 g |
| Thesit (polyethylene glycol monododecyl ether) | — | 1.0 g | — | — | — | — | — |
| water ad | 50.0 g | 50.0 g | 50.0 g | 50.0 g | 50.0 g | 50.0 g | 50.0 g |

EXAMPLE 2.

Water-in-oil emulsion systems 0.1–0.5% Nitrofurantoin monohydrate with a particle size of <10 μm. is emulsified, with stirring and warming, in 0.5–10% of a water-oil emulsifier or 20–50% of a non-ionic emulsifier, oily fats in an amount of 3–15%, as well as 3–15% glycerol or polyethylene glycol 400, together with 35–65% of water, in which 0.1–0.5% methyl cellulose has been pre-swollen. There are thus obtained water-in-oil emulsions which have a good compatibility.

The formulations given in the following Table 2 have proved to be especially useful:

TABLE 2

| component | amount | | | | |
|---|---|---|---|---|---|
| | H | I | J | K | L |
| lidocaine hydrochloride | 30.0 mg | 30.0 mg | 30.0 mg | 30.0 mg | 30.0 mg |
| nitrofurantoin monohydrate | 100.0 mg | 100.0 mg | 100.0 mg | 100.0 mg | 100.0 mg |
| Protegin X (paraffin hydrocarbons with hydroxycholesterol) | 2.5 g | 3.0 g | 5.0 g | 3.0 g | 10.0 g |
| Miglyol 812 (triglyceride mixture of low viscosity) | 15.0 g | 15.0 g | 15.0 g | 8.0 g | 3.0 g |
| polyethylene glycol 400 | 10.0 g | 10.0 g | 10.0 g | 5.0 g | — |
| glycerol | — | — | — | — | 3.0 g |

TABLE 2-continued

| component | amount | | | | |
|---|---|---|---|---|---|
| | H | I | J | K | L |
| Culminal K 42 (methyl cellulose) | 0.1 g | 0.1 g | 0.1 g | 0.2 g | 0.1 g |
| water ad | 50.0 g | 50.0 g | 50.0 g | 50.0 g | 50.0 g |

EXAMPLE 3.

Oil-in-water emulsion systems with partly dissolved active material.

0.5-2% Nalidixic acid is partly dissolved in 25 g. water, together with xylocaine hydrochloride, and the swelling material incorporated therein. 0.5-10% of a non-ionic or 0.1-0.5% of an ionic oil-in-water emulsifier, polyethylene glycol, as well as an appropriate lipophilic phase, are emulsified together with the hydrophilic phase. There are thus obtained oil-in-water instillation emulsions of good compatibility.

The formulations given in the following Table 3 have proved to be especially useful:

TABLE 3

| Component | amount | |
|---|---|---|
| | M | N |
| nalidixic acid | 500.0 mg | 500.0 mg |
| xylocaine hydrochloride | 30.0 mg | 30.0 mg |
| polyethylene glycol 400 | 20.0 g | 10.0 g |
| Miglyol 812 (oily triglyceride mixture) | 5.0 g | 3.0 g |
| Myrj 52 (polyoxyethylene stearate) | 0.5 g | — |
| Tegin (glycerol stearate) | — | 6.0 g |
| methyl cellulose | 0.4 g | 0.4 g |
| water ad | 50.0 g | 50.0 g |

EXAMPLE 4.

Oil-in-water emulsion system with very sparingly soluble active materials 0.5-3% of a quinolone or pyridazine derivative with a particle size of <10 μm. are stirred into an emulsion which is prepared as follows:

0.5-10% of a non-ionic or 0.1 to 5% of an ionic oil-in-water emulsifier are, with the addition of polyethylene glycol and of an appropriate lipophilic phase, worked up to give an emulsion with 60-80% of water in which a swelling material has been pre-swollen, by stirring and possibly with warming.

The formulations given in the following Table 4 have proved to be especially useful:

TABLE 4

| component | amount | | |
|---|---|---|---|
| | O | P | Q |
| 1-(β-chloroethyl)-3-ethoxy-carbonyl-1,4-dihydrocyclopenteno(h)quinolone | 1.0 g | — | — |
| 1-ethyl-3-ethoxy-carbonyl-1,4-dihydrocyclopenteno-(h)quinolone | — | 1.0 g | — |
| 8-(1-methyl-5-nitro-2-imidazolyl)-6-amino-s-triazolo[3,4-s]-pyridazine | — | — | 1.0 g |
| polyethylene glycol 400 | 20.0 g | 20.0 g | 20.0 g |
| Miglyol 812 (oily viscous triglyceride mixture) | 5.0 g | 10.0 g | 10.0 g |
| Myrj 52 (polyoxyethylene stearate | 0.5 g | — | — |
| Tegin (glycerol stearate) | — | 2.5 g | 5.0 g |
| methyl cellulose | 0.4 g | 0.3 g | 0.3 g |
| water ad | 50.0 g | 50.0 g | 50.0 g |

It will be appreciated that the instant specification and examples are set forth by way of illustration and not limitation, and that various modifications and changes may be made without departing from the spirit and scope of the present invention.

What we claim is:

1. An installation composition in the form of a low viscosity triglyceride oil-in-water emulsion consisting essentially of about 60 to 90% by weight of water, 10 to 30% by weight of the triglyceride oil, 0.3 to 3% by weight of a polysaccharide derivative swelling agent, 0.5 to 10% by weight of a non-ionic emulsifier and an antibacterially effective amount of nitrofurantoin of a particle size of less than about 10 μm suspended therein.

2. A unit dose of an installation composition according to claim 1 of a volume of up to about 50 ml.

3. An installation composition in the form of a water-in-low viscosity triglyceride oil emulsion consisting essentially of about 35 to 65% by weight of water, 3 to 15% by weight of the triglyceride oil, 3 to 15% by weight of glycerol or polyethylene glycol, 20 to 50% by weight of a non-ionic emulsifier and an antibacterially effective amount of nitrofurantoin of a particle size of less than about 10 μm suspended therein.

4. A unit dose of an installation composition according to claim 3 of a volume of up to about 50 ml.

* * * * *

UNITED STATES PATENT AND TRADEMARK OFFICE
CERTIFICATE OF CORRECTION

PATENT NO. : 4,191,772
DATED : March 4, 1980
INVENTOR(S) : Heinrich Woog et al

It is certified that error appears in the above-identified patent and that said Letters Patent are hereby corrected as shown below:

Inventors: Rothe is from Hockenheim not Hackenheim.

Column 6, line 18, Table 4: "8-(1-methyl-5-nitro-2-"

should be "3-(1-methyl-5-nitro-2-".

Column 6, line 35 "installation" should be instillation".

Column 6, line 45, "installation" should be "instillation".

Signed and Sealed this

Twenty-eighth Day of October 1980

[SEAL]

Attest:

SIDNEY A. DIAMOND

Attesting Officer

Commissioner of Patents and Trademarks